US00PP31318P2

(12) United States Plant Patent
Dirr et al.

(10) Patent No.: US PP31,318 P2
(45) Date of Patent: Jan. 7, 2020

(54) ***ITEA* PLANT NAMED 'BAILTEAONE'**

(50) Latin Name: *Itea virginica*
Varietal Denomination: Bailteaone

(71) Applicant: Bailey Nurseries Inc, Newport, MN (US)

(72) Inventors: Michael A. Dirr, Bogart, GA (US); Rhonda Helvick, Madison, GA (US); Oren McBee, Bishop, GA (US)

(73) Assignee: BAILEY NURSERIES, INC., Newport, MN (US)

( * ) Notice: Subject to any disclaimer, the term of this patent is extended or adjusted under 35 U.S.C. 154(b) by 0 days.

(21) Appl. No.: 16/350,776

(22) Filed: Jan. 9, 2019

(51) Int. Cl.
*A01H 5/02* (2018.01)

(52) U.S. Cl.
USPC ..... Plt./226

(58) Field of Classification Search
USPC ..... Plt./226
CPC ..... A01H 5/02
See application file for complete search history.

*Primary Examiner* — Annette H Para
(74) *Attorney, Agent, or Firm* — Penny J. Aguirre

(57) ABSTRACT

A new cultivar of *Itea* plant named 'Bailteaone' that is characterized by its compact and rounded to upright habit, its prolific blooming habit with white star shaped flowers on numerous racemes, its freely branched habit, its excellent vigor, and its vibrant red maroon fall color.

2 Drawing Sheets

Botanical classification: *Itea virginica.*
Variety denomination: 'Bailteaone'.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1).

BACKGROUND OF THE INVENTION

The present invention relates to a new and distinct cultivar of *Itea virginica*. The new *Itea* will hereafter be referred to by its cultivar name, 'Bailteaone'. 'Bailteaone' is a new cultivar of *Itea virginica* grown for use as an ornamental landscape plant.

The new cultivar was derived from a controlled breeding program conducted by the Inventors in Watkinsville, Ga. 'Bailteaone' arose from a controlled cross made in 2008 between *Itea virginica* 'Henry's Garnet' (not patented) as the female parent and *Itea virginica* 'Sarah Eve' (not patented) as the male parent. 'Bailteaone' was selected as a single unique plant in 2009 from amongst seedlings derived from the above cross.

Asexual propagation of the new cultivar was first accomplished by semi-hardwood stem cuttings by one of the Inventors in Watkinsville, Ga. in 2009. Asexual propagation by semi-hardwood stem cuttings has determined that the characteristics of the new cultivar are stable and are reproduced true to type in successive generations.

SUMMARY OF THE INVENTION

The following traits have been repeatedly observed and represent the characteristics of the new cultivar. The attributes in combination distinguish 'Bailteaone' as a unique cultivar of *Itea.*

1. 'Bailteaone' exhibits a compact and rounded to upright habit.
2. 'Bailteaone' exhibits a prolific blooming habit with white star shaped flowers on numerous racemes.
3. 'Bailteaone' exhibits a freely branched habit.
4. 'Bailteaone' exhibits excellent vigor.
5. 'Bailteaone' exhibits vibrant red maroon fall color.

The female parent plant differs from 'Bailteaone' in having a less compact and less uniform plant habit (more unruly), a less vigorous growth habit, less prolific blooming habit, and less intense fall foliage color. The male parent plant differs from 'Bailteaone' in having sepals and pedicels that are pink-purple in color, a less vigorous growth habit, and less significant fall color. 'Bailteaone' can also be compared to *Itea virginica* cultivar 'Sprich' (U.S. Plant Pat. No. 10,988). 'Sprich' differs from 'Bailteaone' in having a much less vigorous growth habit and a smaller plant size.

BRIEF DESCRIPTION OF THE DRAWINGS

The accompanying colored photographs illustrate the overall appearance and distinct characteristics of the new *Itea*. The photographs in the figures were taken of a plant 2 years in age as grown outdoors in a trial garden in Watkinsville, Ga.

The photograph in FIG. 1 provides a side view of a plant of 'Bailteaone' in bloom.

Figure 1:
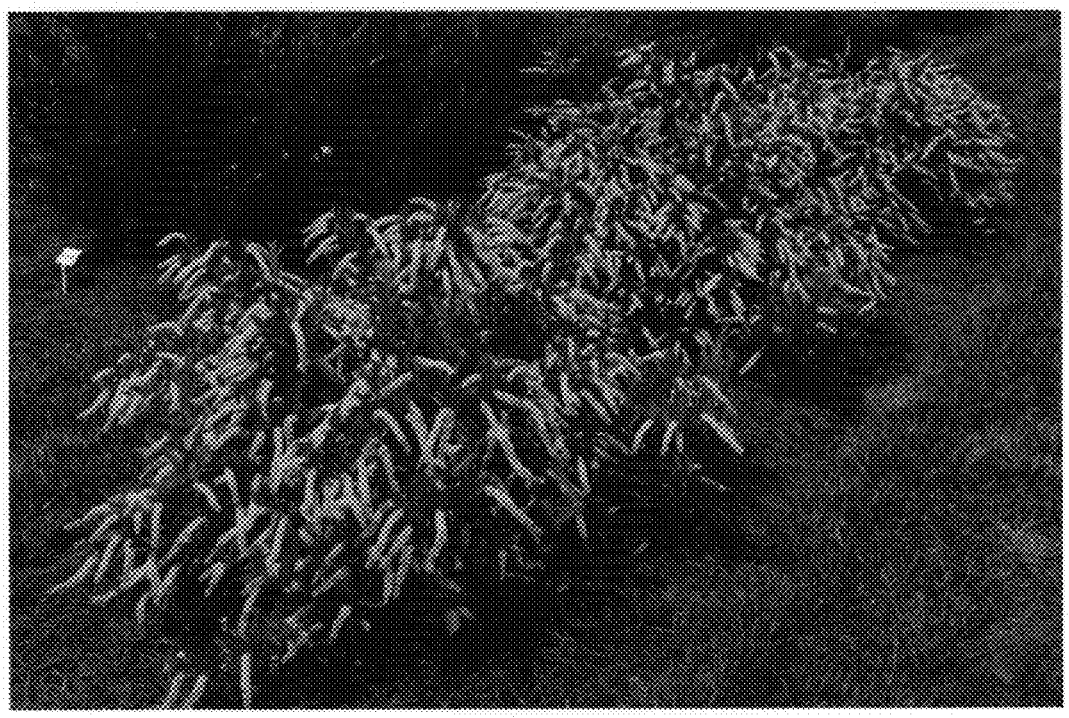
Figure 2:
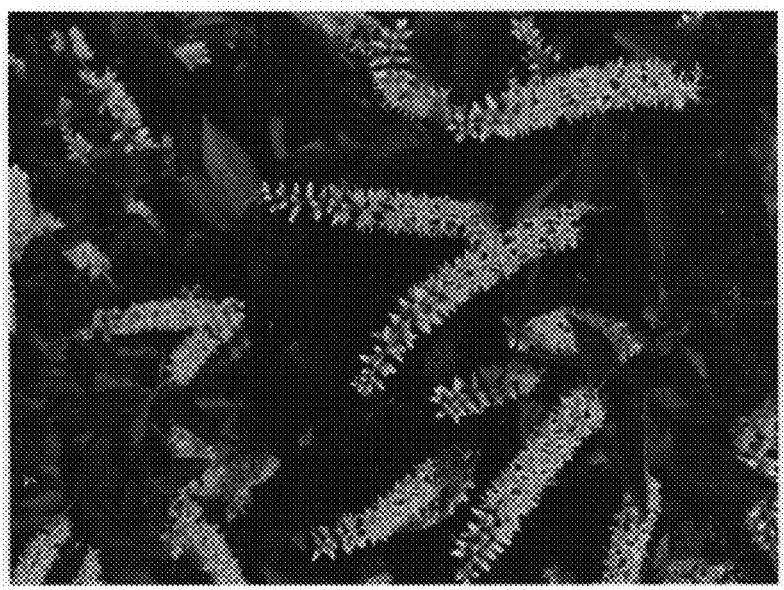

The photograph in FIG. 2 provides a close-up view of the inflorescences of 'Bailteaone'.

Figure 3:
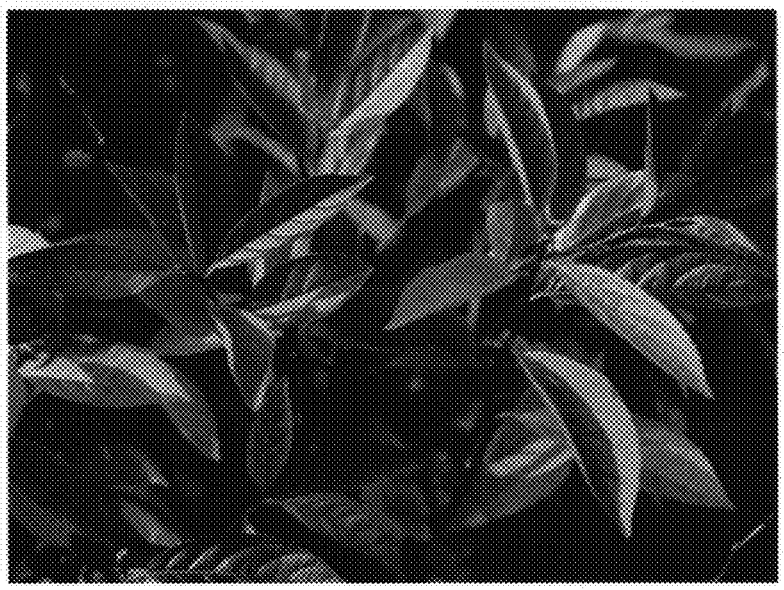

The photograph in FIG. 3 provides a close-up view of the fall color of 'Bailteaone'.

The colors in the photographs are as close as possible with the digital photography and printing techniques utilized and the color codes in the detailed botanical description accurately describe the colors of the new *Itea*.

DETAILED BOTANICAL DESCRIPTION

The following is a detailed description of plants 2 years in age as grown outdoors in a trail garden in Watkinsville, Ga.

The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Late spring to early summer in Watkinsville, Ga.

*Plant type.*—Deciduous flowering shrub.

*Plant habit.*—Compact and rounded to upright plant habit.

*Height and spread.*—An average of 75 cm in height and 100 cm in width as a 2-year-old plant in the landscape.

*Hardiness.*—U.S.D.A. Zones 5 to 9.

*Diseases and pests.*—No susceptibility or resistance to diseases or pests has been observed.

*Root description.*—156A, in color, roots fine and freely branching.

*Propagation.*—Semi-hardwood stem cuttings.

*Root development.*—An average of 6 weeks at 32° C. for root initiation and an average of 3 months at 32° C. to produce a young rooted plant.

*Growth rate.*—Vigorous.

Branch description:

*Branch strength.*—Young; flexible and strong, mature; easily broken.

*Branch aspect.*—Held at angles ranging between 45° and 75°.

*Branch shape.*—Rounded.

*Branch color.*—Main and lateral branches; first year 178A, second year and trunk N200B.

*Branch surface.*—Main and lateral branches; first year covered with tomentulose pubescence, second year glabrous, trunk, fine barked.

*Branch size.*—Main branches; first year 27 cm in length, 3 mm in diameter, second year 45 cm in length, 5 mm in diameter, lateral branches; 15 cm in length, 5 mm in diameter, trunk; multi-branched and 4 cm in diameter at soil level.

*Branching habit.*—Freely and multi branching habit, pruning enhances lateral development, an average of 15 lateral branches on a 2-year-old plant.

*Internode length.*—1 to 4 cm.

*Vegetative buds.*—Superposed, upper larger than the basal, imbricate, an average of 3 mm in length and 1 mm in width, 143C in color.

Foliage description:

*Leaf number.*—An average of 15 to 20 per branch.

*Leaf arrangement.*—Alternate.

*Leaf shape.*—Elliptic.

*Leaf size.*—4 to 7 cm in length and 2 to 3 cm in width.

*Leaf division.*—Simple, generally symmetrical, abundant, alternate and flat in aspect.

*Leaf base.*—Acute.

*Leaf apex.*—Acute to slightly acuminate.

*Leaf margin.*—Serrulate.

*Leaf venation.*—Pinnate, upper surface 144A, lower surface 144C.

*Leaf attachment.*—Petiolate.

*Leaf surface.*—Both surfaces smooth, upper surface; glabrous and lustrous, lower surface; sparingly pubescent.

*Leaf color.*—Young upper surface 144A, young lower surface 144B, mature upper surface 147A, mature lower surface 147B, fall leaf color; 59A, or 64A, or a blend of 59A and 64A on both surfaces.

*Petioles.*—9 to 10 mm in length and 1.5 mm in diameter, pubescent, grooved on upper side, color 144A.

Flower description:

*Inflorescence type.*—Cylindrical drooping racemes, which cover the shrub with bloom in late spring to early summer.

*Inflorescence size.*—An average of 10 cm in height and 1.25 cm in width.

*Lastingness of inflorescence.*—Inflorescence are showy for an average of 3 to 4 weeks; individual flowers last an average of 2 days, freely and continuously flowering with numerous recements in flower simultaneously, flower development on an individual raceme occurs of several weeks and commences at the base of the raceme and progresses towards the apex.

*Inflorescence quantity.*—13 to 20 per lateral branch.

*Fragrance.*—Fragrant.

*Quantity of flowers.*—An average of 200 flowers per inflorescence.

*Flower type.*—Star shaped flowers arranged on terminal racemes.

*Flower size.*—An average of 5 mm in height and 3 mm in diameter.

*Flower buds.*—Conical to ovate in shape, length about 2 to 6 mm, diameter about 2 to 3 mm, surface is glabrous and 149D in color.

*Flower aspect.*—Held upright, horizontal, or curving and pendulous.

*Pedicel.*—Strong, average of 3 mm in length and 1 mm in diameter, N144B in color, surface is tomentulose.

*Peduncle.*—Average of 1 to 3 cm in length, N144B in color, glabrous surface.

*Petals.*—5, average of 4 mm in length, 1 mm in width, linear in shape, acute apex, entire margin, color when opening upper surface 155D, when opening lower surface 155D, mature upper surface 155D, mature lower surface 155D.

*Calyx.*—Turbinate with five lobes, average of 1 mm in length, 2 to 3 mm in diameter, color on upper and lower surface N144B.

Reproductive organs:

*Gynoecium.*—Pistil; 1 inferior, average of 3 mm in length and N144B in color, glabrous surface, style; average of 3 mm in length and 144B in color, stigma; grooved, 1 mm in width and N144B in color, ovary; 10D in color and 1 mm in diameter.

*Androecium.*—Stamens; 5, average of 4 mm in length, glabrous surface, anther; 10A in color, filaments; N144B in color, pollen; is moderate in quantity and 10A in color.

*Fruit and seed.*—Fruit; Two-grooved capsules, occurring in racemes that are persistent through the winter, an average of 7 mm in length and 2 mm in diameter, 138A in color when immature and N199A in color when mature, seed; numerous, 1 mm in length and 5 mm in width, 203B in color.

It is claimed:

1. A new and distinct cultivar of *Itea* plant named 'Bailteaone' as herein illustrated and described.

* * * * *